United States Patent [19]

Katz et al.

[11] 4,353,908

[45] Oct. 12, 1982

[54] SELECTED 2-TRICHLOROMETHYL-4-PYRIMIDINYL CARBONATES AND THEIR USE AS FUNGICIDES

[75] Inventors: Lawrence E. Katz, Orange; Walter A. Gay, Cheshire, both of Conn.

[73] Assignee: Olin Corporation, New Haven, Conn.

[21] Appl. No.: 321,033

[22] Filed: Nov. 13, 1981

[51] Int. Cl.$^3$ .................... A01N 43/54; C07D 239/36
[52] U.S. Cl. .................................... 424/251; 544/319
[58] Field of Search ......................... 544/319; 424/251

[56] References Cited

FOREIGN PATENT DOCUMENTS 2734827  2/1978  Fed. Rep. of Germany ...... 544/319

Primary Examiner—Robert Gerstl

Attorney, Agent, or Firm—William A. Simons; Thomas P. O'Day

[57] ABSTRACT

Disclosed are selected 2-trichloromethyl-4-pyrimidinyl carbonates having the formula:

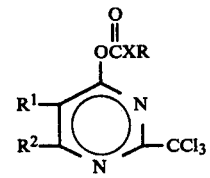

wherein X is an atom selected from the group consisting of oxygen and sulfur; R is a lower alkyl group having 1 to 4 carbon atoms or a phenyl group; $R^1$ is hydrogen or halo; and $R^2$ is a lower alkyl group having 1 to 4 carbon atoms. These compounds are disclosed to be agricultural fungicides.

26 Claims, No Drawings

SELECTED 2-TRICHLOROMETHYL-4-PYRIMIDINYL CARBONATES AND THEIR USE AS FUNGICIDES

BACKGROUND OF THE INVENTION

1. Field of the Invention

This invention relates to selected 2-trichloromethyl-4-pyrimidinyl carbonates and their use as fungicides.

2. Description of the Prior Art

British Patent No. 1,181,657 discloses the use of 5,6-dimethyl-2-dimethylamino-4-pyrimidinyl dimethylcarbamate as an insecticide.

BRIEF SUMMARY OF THE INVENTION

Accordingly, the present invention is directed to, as compositions of matter, selected 2-trichloromethyl-4-pyrimidinyl carbonates having the formula:

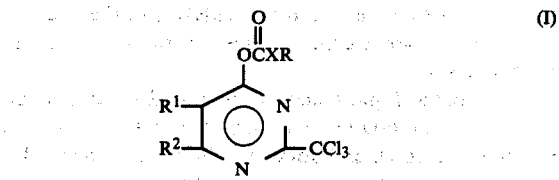

wherein X is an atom selected from the group consisting of oxygen and sulfur; R is a lower alkyl group having 1 to 4 carbon atoms or a phenyl group; $R^1$ is hydrogen or halo; and $R^2$ is a lower alkyl group having 1 to 4 carbon atoms. It is to be understood that the term "halo" as used in the specification and claims herein is intended to include fluoro, chloro, bromo, and iodo. The present invention is also directed to the use of these compounds as fungicides.

DETAILED DESCRIPTION

The pyrimidinyl carbonate compounds of the present invention may be prepared by reacting trichloroacetamidine with a selected acetoacetate to form the corresponding 4-hydroxy-2-trichloromethylpyrimidine, which is then reacted with a selected chloroformate. These general reactions are illustrated below in equations (A) and (B). In equation (A), trichloroacetamidine is reacted with methyl acetoacetate to form 4-hydroxy-6-methyl-2-trichloromethylpyrimidine. In equation (B), the 4-hydroxy-6-methyl-2-trichloromethylpyrimidine is reacted with phenyl chloroformate to form 6-methyl-4-phenoxycarbonyloxy-2-trichloromethylpyrimidine.

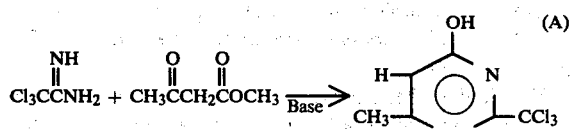

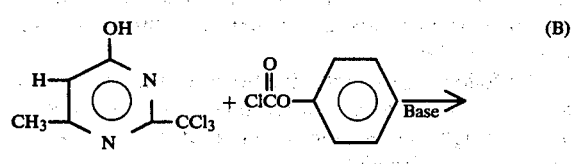

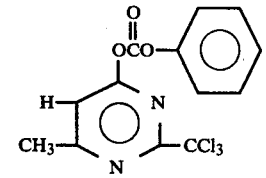

The trichloroacetamidine reactant is made by reacting trichloroacetonitrile with ammonia. Trichloroacetonitrile is a commercially available material. See German Patent No. 671,785.

The acetoacetate reactants may be made by reacting the corresponding acetate with a suitable condensing agent such as sodium ethoxide. See Hickenbottom, W. J., *Reactions of Organic Compounds* (3rd Edition), pages 359 and 360 (1957). For example, ethyl acetate may be treated with sodium ethoxide, and the resulting mixture acidified to form ethyl acetoacetate. Various acetoacetates such as methyl acetoacetate and ethyl acetoacetate are commercially available.

Illustrative acetoacetate reactants for the compounds of the present invention include the following:
methyl acetoacetate;
ethyl acetoacetate;
ethyl 2-chloroacetoacetate;
ethyl butyrylacetate.

The chloroformate reactants may be made by reacting the corresponding alcohol or thiol with phosgene. See *Rodd's Chemistry of Carbon Compounds*, Coffey, S. (editor), Vol. 1, Part C, pages 276–9 (1965). For example, phenol may be reacted with phosgene to produce phenyl chloroformate. Various chloroformates such as ethyl chloroformate and phenyl chloroformate are commercially available.

Illustrative chloroformate reactants for the compounds of the present invention include the following:
methyl chloroformate;
ethyl chloroformate;
isopropyl chloroformate;
phenyl chloroformate;
s-ethyl chlorothioformate.

Any suitable conventional reaction conditions may be employed in the synthesis of the 4-hydroxy-2-trichloromethylpyrimidine compounds. See Henze et al., *J. Org. Chem.*, 17, 1320 (1952); Falch et al., *J. Med. Chem.*, 11, 608 (1968); and U.S. Pat. No. 3,118,889 as examples of such a synthesis.

A wide variety of conventional reaction conditions may be employed in the synthesis of the present compounds according to equation (B) and the present invention is not intended to be limited to any particular reaction conditions. For example, acylation of the hydroxyl group of the 4-hydroxy-2-trichloromethylpyrimidine compound can be carried out by reacting the 4-hydroxy-2-trichloromethylpyrimidine compound with a selected chloroformate in the presence of a base such as triethylamine, pyridine, sodium carbonate or potassium carbonate. Alternatively, the 4-hydroxy-2-trichloromethylpyrimidine compound can be reacted with phosgene and a selected alcohol or thiol. Advantageously and preferably, the reactions are performed with at least a molar amount of chloroformate to the 4-hydroxy-2-trichloromethylpyrimidine compound (e.g. from about 0.0 to about 1.0 mole excess). It is also preferred to use an equimolar amount of the base to the chloroformate, although lesser or greater amounts can be employed. A solvent is not necessary, but any suitable inert solvent such as acetonitrile or diethyl ether may be employed.

Furthermore, the reaction temperature and time will both depend upon many factors including the exact reactants being employed. In most situations, reaction temperatures from about 30° C. to about 100° C. and reaction times from about 2 hours to about 72 hours are preferred.

The desired product may be recovered from the reaction mixture by any conventional means, for example, extraction, recrystallization, or the like. Finally, it should be noted that while the reactions illustrated by equations (A) and (B) are preferred, other synthesis methods for preparing compounds of the present invention may also be employed.

Representative compounds of the present invention include the following:
4-ethoxycarbonyloxy-6-methyl-2-trichloromethylpyrimidine;
5-chloro-4-ethoxycarbonyloxy-6-methyl-2-trichloromethylpyrimidine;
4-isopropoxycarbonyloxy-6-methyl-2-trichloromethylpyrimidine;
6-methyl-4-phenoxycarbonyloxy-2-trichloromethylpyrimidine;
4-ethoxycarbonylthio-6-methyl-2-trichloromethylpyrimidine.

Also, in accordance with the present invention, it has been found that the compounds of Formula (I) above may be utilized as effective foliar fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar fungi when either employed by itself (i.e., in full concentration) or in sufficient concentrations within a carrier or other substance. Of course, this amount may be constantly changing because of the possible variations in many parameters. Some of these may include: the number and type of fungi to be controlled or killed; the type of media to which the present compound can be applied (e.g., seedlings or fully grown plants); degree of effectiveness required; and type of carrier, if any. Generally speaking, applications of an aqueous spray containing at least about 5, more preferably in the range of about 30 to 300, parts per million of the chemical of the present invention may give satisfactory fungi control.

This step of contacting may be accomplished by applying this compound to the fungi themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compounds may be broadened by the addition thereto of other known pesticides such as other fungicides, herbicides, insecticides, and the like.

Specific methods of formulating and applying these active compounds include applying them in the form of dusts, dust or emulsion concentrates, wettable powders and concentrates, granulates, dispersions, sprays, solutions, and the like.

The dusts are usually prepared by simply grinding together from about 1% to about 15% by weight of the active compound with a finely divided inert diluent such as walnut flour, diatomaceous earth, fullers earth, attaclay, talc, or kaolin. Dust concentrates are made in similar fashion except that about 16% to about 75% by weight of active compound is ground usually together with the diluent. In practice, dust concentrates are then generally admixed at the site of use with more inert diluent before it is applied to the plant foliage, soil or animals which are to be protected from fungi attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals, and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic or aromatic hydrocarbon or their derivatives. It is preferred that the solvent be odorless and, moreover, be inert to the active compound.

It should be clearly understood that the fungicide formulations, the ingredients which may make up such formulations other than the active compound, the dosages of these ingredients, and means of applying these formulations may include all known and conventional substances, amounts, and means, respectively, that are suitable for obtaining the desired fungicidal result. And, therefore, such process parameters are not critical to the present invention.

Fungicides of the present invention may be effective for the control of broad classes of foliar fungi. Specific illustrations of foliar fungi wherein fungicidal activity has been shown include cucumber anthracnose and downey mildew.

The following examples further illustrate the present invention. All parts and percentages employed therein are by weight unless otherwise indicated. Yields given are percent molar yields.

EXAMPLE 1

Preparation of 4-Hydroxy-6-Methyl-2-Trichloromethylpyrimidine

A mixture of 44.4 g (0.28 mole) trichloroacetamidine, 32.0 g (0.28 mole) methyl acetoacetate, 37.5 g (0.28 mole) potassium carbonate, and 450 ml water was stirred for 3 days. A trace of solid was removed by filtration and the filtrate was made acidic with hydrochloric acid. The product precipitated out to give 28.9 g (46% yield; mp 173°–174° C.). The structure was confirmed via mp*, infrared, and elemental analysis.
*J. Med. Chem., 11, 608 (1968).

|  | Analysis for $C_6H_5N_2Cl_3O$: | | | |
|---|---|---|---|---|
|  | C | H | N | Cl |
| Calculated: | 31.68 | 2.22 | 12.32 | 46.76 |
| Found: | 31.37 | 2.26 | 12.31 | 46.86 |

EXAMPLE 2

Preparation of 6-Methyl-4-Phenoxycarbonyloxy-2-Trichloromethylpyrimidine

To 5.6 g (0.02 mole) 4-hydroxy-6-methyl-2-trichloromethylpyrimidine, 2.0 g (0.02 moles) triethylamine, and 100 ml ether was added 3.2 g (0.07 mole) phenyl chloroformate. The solution refluxed on addition and a precipitate formed. This was stirred 0.5 hour, filtered, and the filtrate rotary evaporated to give 6.6 g (76% yield) thick oily residue. Extraction with ligroin gave, on cooling of the extract, 3.7 g pure product as a viscous oil. The structure was confirmed via infrared and elemental analysis.

|  | Analysis for $C_{13}H_9N_2Cl_3O_3$: | | | |
|---|---|---|---|---|
|  | C | H | N | Cl |
| Calculated: | 44.88 | 2.61 | 8.11 | 30.60 |
| Found: | 44.81 | 2.55 | 8.12 | 30.42 |

EXAMPLE 3

Preparation of 4-Ethoxycarbonylthio-6-Methyl-2-Trichloromethylpyrimidine

A solution of 5.6 g (0.02 mole) 4-hydroxy-6-methyl-2-trichloromethylpyrimidine, 2.0 (0.02 mole) triethylamine, 2.5 g (0.02 mole) s-ethyl chlorothioformate, and 100 ml ether was refluxed 18 hours. The mixture was filtered and the filtrate rotary evaporated to give a residue which was taken up in ligroin. On cooling 0.7 g starting material (mp 170°–172° C.) was recovered. On concentration 4.3 g (63% yield) of product was isolated. An analytical sample was prepared by recrystallization from ligroin, mp 33°–34.5° C. The structure was confirmed via infrared and elemental analysis.

|  | Analysis for $C_9H_9N_2Cl_3SO_2$: | | | | |
|---|---|---|---|---|---|
|  | C | H | N | Cl | S |
| Calculated: | 34.25 | 2.87 | 8.88 | 33.70 | 10.16 |
| Found: | 34.03 | 2.72 | 9.19 | 33.90 | 9.93 |

EXAMPLE 4

Preparation of 5-Chloro-4-Hydroxy-6-Methyl-2-Trichloromethylpyrimidine

A mixture of 30.0 g (0.18 mole) trichloroacetamidine, 25.2 g (0.18 mole) potassium carbonate, 30.3 g (0.18 mole) ethyl 2-chloroacetoacetate, and 300 ml water was stirred 18 hours. The aqueous solution was decanted from heavier tars and acidified with hydrochloric acid. The precipitate that was formed was filtered, washed, and dried to give 14.7 g (31% yield; mp 130°–145° C.) of crude product. An analytical sample was prepared by recrystallization from cyclohexane (mp 156°–157° C.). The structure was confirmed via infrared and elemental analysis.

|  | Analysis for $C_6H_4N_2Cl_4O$: | | | |
|---|---|---|---|---|
|  | C | H | N | Cl |
| Calculated: | 27.51 | 1.54 | 10.74 | 54.15 |
| Found: | 28.20 | 1.88 | 11.00 | 52.54 |

EXAMPLE 5

Preparation of 5-Chloro-4-Ethoxycarbonyloxy-6-Methyl-2-Trichloromethylpyrimidine To a solution of 5.8 g (0.02 mole) 5-chloro-4-hydroxy-6-methyl-2-trichloromethylpyrimidine, 2.0 g (0.02 mole) triethylamine, and 100 ml ether was added 2.2 g (0.02 mole) ethyl chloroformate. An immediate reaction ensued and a precipitate formed. After refluxing 2 hours longer the mixture was filtered, and the filtrate was washed with aqueous potassium carbonate and then with water. Rotary evaporation yielded 5.4 g residue which was recrystallized from ligroin to give 4.6 g (69% yield) of pure product (mp 43.5°–44.5° C.). The structure was confirmed via infrared and elemental analysis.

|  | Analysis for $C_9H_8N_2Cl_4O_3$: | | | |
|---|---|---|---|---|
|  | C | H | N | Cl |
| Calculated: | 32.36 | 2.41 | 8.39 | 42.46 |
| Found: | 32.26 | 2.61 | 8.51 | 42.20 |

EXAMPLE 6

Preparation of 4-Ethoxycarbonyloxy-6-Methyl-2-Trichloromethylpyrimidine

To a solution of 3.0 g (0.013 mole) 4-hydroxy-6-methyl-2-trichloromethylpyrimidine, 1.4 g (0.013 mole) triethylamine, and 75 ml ether was added 1.4 g (0.013 mole) ethyl chloroformate. The reaction mixture was refluxed for 2 hours, filtered, and rotary evaporated under aspiration to give a dark oil. This was triturated with petroleum ether and the solution decanted from tars. The solvent was stripped in vacuo and the product distilled to give 2.7 g (67% yield; $bp_{0.5\ mm}$ 125° C.). The structure was confirmed via infrared and elemental analysis.

| Analysis for $C_9H_9N_2Cl_3O_3$: | | | |
|---|---|---|---|
| | C | H | N | Cl |
| Calculated: | 40.64 | 3.07 | 9.48 | 35.99 |
| Found: | 40.39 | 3.20 | 9.60 | 36.27 |

EXAMPLE 7

Preparation of 4-Isopropoxycarbonyloxy-6-Methyl-2-Trichloromethylpyrimidine

To a solution of 3.0 g (0.013 mole) 4-hydroxy-6-methyl-2-trichloromethylpyrimidine, 1.4 g (0.013 mole) triethylamine, and 75 ml ether was added 1.6 g (0.013 mole) isopropyl chloroformate. The reaction mixture was refluxed one hour, filtered, and rotary evaporated to give a yellow oil. The oil was distilled (bp$_{1.2 mm}$ 120° C.) to give a cloudy yellow oil. This was taken up in benzene, filtered, and the solvent removed leaving 2.4 g (57% yield) of product. The structure was confirmed via infrared and elemental analysis.

| Analysis for $C_{10}H_{11}N_2Cl_3O_3$: | | | |
|---|---|---|---|
| | C | H | N | Cl |
| Calculated: | 38.30 | 3.54 | 8.93 | 33.92 |
| Found: | 38.22 | 3.66 | 8.90 | 33.97 |

Foliar Fungicide Screen

The active materials formed in Examples 2, 3, 5, 6, and 7 were tested for activity as effective fungicides.

A uniform aqueous dispersion of each chemical made in the above examples was first prepared. These dispersions were made by dissolving each chemical in a solution of acetone containing the surfactant TRITON X-155[1] (concentration 500 parts per million). Next, this solution was diluted with water (1:9) to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1] Manufactured by Rohm and Haas of Philadelphia, Pennsylvania and is a polyether alcohol.

The aqueous solutions containing each chemical were applied to various plants according to the methods stated below. These tests were designed to evaluate the ability of the chemical to protect non-infected foliage and eradicate recently established infection against major types of fungi such as anthracnose and mildew that attack above-ground parts of plants.

Cucumber Anthracnose

Two week old cucumber plants were sprayed while rotating the plants on a turntable with an aqueous solution that contained 260 parts per million by weight of the active chemicals of Examples 2, 3, 5, and 6. Simultaneously, the soil in each pot was drenched with an aqueous dispersion of each chemical in the amount of 25 lb/acre. After the spray deposit had dried, the plants were atomized with a suspension of cucumber anthracnose spores (*Collectotrichum lagenarium*) and placed in a moist chamber at 70° F. for 24 hours. After 5 days in a greenhouse, the severity of pustule formation was rated on a scale of 0 (no inhibition) to 10 (complete inhibition). Subsequent tests were conducted as described, except that the materials were tested for control at lower dosages and the drench and spray applications were done separately. See Table I for the results of these tests.

TABLE I

| | FUNGICIDAL ACTIVITY AGAINST CUCUMBER ANTHRACNOSE | | | | | | |
|---|---|---|---|---|---|---|---|
| Compound | 25 lb/acre drench & 260 ppm spray | 12.5 lb/acre drench | 6.3 lb/acre drench | 3.2 lb/acre drench | 130 ppm spray | 65 ppm spray | 33 ppm spray |
| Example 2 | 8 | 7 | 3 | 6 | 2 | 5 | 0 |
| Example 3 | 6 | 0 | — | — | — | — | — |
| Example 5 | — | — | — | 4 | 6 | 8 | 6 |
| Example 6 | 8 | — | — | — | — | — | — |

Downey Mildew

Soybean plants were sprayed with solutions of the active chemicals of Examples 2, 3, 5, and 7 at 260 ppm by weight and simultaneously the soil drenched with the chemical at 25 lb/acre. Lower concentrations, if examined, were tested separately as a spray at 130 and 65 ppm, and as a drench at 12.5 lb/acre. After the spray deposit had dried, the plants were atomized with a suspension of *Peronospora manshurica* and placed in a moist chamber at 65° F. for 1 day. After 5 days in a greenhouse, the severity of infection was rated on a scale of 0 (no inhibition) to 10 (complete inhibition). See Table II for the results of these tests.

TABLE II

| | FUNGICIDAL ACTIVITY AGAINST DOWNEY MILDEW | | | |
|---|---|---|---|---|
| Compound | 25 lb/acre drench & 260 ppm spray | 12.5 lb/acre drench | 130 ppm spray | 65 ppm spray |
| Example 2 | 8 | 5 | 2 | 3 |
| Example 3 | 9 | 0 | 6 | 2 |
| Example 5 | 9 | 1 | 5 | 5 |
| Example 7 | 10 | — | — | — |

What is claimed is:

1. A compound having the formula:

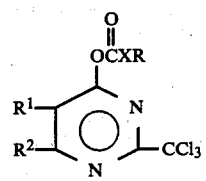

wherein X is an atom selected from the group consisting of oxygen and sulfur; R is a lower alkyl group having 1 to 4 carbon atoms or a phenyl group; $R^1$ is hydrogen or halo; and $R^2$ is a lower alkyl group having 1 to 4 carbon atoms.

2. The compound of claim 1 wherein X is oxygen.

3. The compound of claim 2 wherein R is a lower alkyl group having 1 to 4 carbon atoms.

4. The compound of claim 3 wherein $R^1$ is hydrogen.

5. The compound of claim 3 wherein $R^1$ is halo.

6. The compound of claim 2 wherein R is a phenyl group.

7. The compound of claim 6 wherein $R^1$ is hydrogen.

8. The compound of claim 6 wherein $R^1$ is halo.

9. The compound of claim 1 wherein X is sulfur.

10. The compound of claim 9 wherein R is a lower alkyl group having 1 to 4 carbon atoms.

11. The compound of claim 10 wherein $R^1$ is hydrogen.

12. The compound of claim 10 wherein $R^1$ is halo.

13. The compound of claim 9 wherein R is a phenyl group.

14. The compound of claim 13 wherein $R^1$ is hydrogen.

15. The compound of claim 13 wherein $R^1$ is halo.

16. A method of controlling fungi which comprises contacting said fungi with a fungicidally effective amount of a compound having the formula:

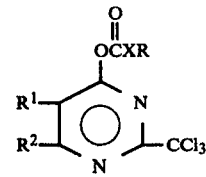

wherein X is an atom selected from the group consisting of oxygen and sulfur; R is a lower alkyl group having 1 to 4 carbon atoms or a phenyl group; $R^1$ is hydrogen or halo; and $R^2$ is a lower alkyl group having 1 to 4 carbon atoms.

17. The method of claim 16 wherein X is oxygen.

18. The method of claim 17 wherein R is a lower alkyl group having 1 to 4 carbon atoms.

19. The method of claim 18 wherein $R^1$ is hydrogen.

20. The method of claim 18 wherein $R^1$ is halo.

21. The method of claim 17 wherein R is a phenyl group.

22. The method of claim 21 wherein $R^1$ is hydrogen.

23. The method of claim 22 wherein said compound is 6-methyl-4-phenoxycarbonyloxy-2-trichloromethyl-pyrimidine.

24. The method of claim 16 wherein X is sulfur.

25. The method of claim 24 wherein R is a lower alkyl group having 1 to 4 carbon atoms.

26. The method of claim 25 wherein $R^1$ is hydrogen.

* * * * *